(12) United States Patent
Brenneman et al.

(10) Patent No.: US 6,911,130 B2
(45) Date of Patent: Jun. 28, 2005

(54) ELECTROCHEMICAL SENSOR

(75) Inventors: Allen J. Brenneman, Goshen, IN (US); Frank W. Wogoman, Granger, IN (US)

(73) Assignee: Bayer HealthCare, LLC, Elkhart, IN (US)

( * ) Notice: Subject to any disclaimer, the term of this patent is extended or adjusted under 35 U.S.C. 154(b) by 180 days.

(21) Appl. No.: 10/010,233

(22) Filed: Dec. 7, 2001

(65) Prior Publication Data

US 2002/0079218 A1 Jun. 27, 2002

Related U.S. Application Data

(60) Provisional application No. 60/254,626, filed on Dec. 12, 2000.

(51) Int. Cl.⁷ ............................................. G01N 27/403
(52) U.S. Cl. .................................. 204/400; 204/403.01
(58) Field of Search ........................... 204/400, 403.01, 204/403.02, 409

(56) References Cited

U.S. PATENT DOCUMENTS 3,773,646 A * 11/1973 Mandle et al. .............. 204/620
5,393,391 A * 2/1995 Dietze et al. ............... 205/781.5
5,997,817 A * 12/1999 Crismore et al. .......... 204/403.1
6,001,228 A * 12/1999 Huber et al. .............. 422/82.01
6,153,070 A * 11/2000 Maurer et al. .............. 204/416

* cited by examiner

Primary Examiner—Kaj K. Olsen
(74) Attorney, Agent, or Firm—Alice A. Brewer

(57) ABSTRACT

An optical reagent format with a precise capillary channel is made by molding a format on a carrier of a precise predetermined thickness. The carrier includes an insert at least a portion of which is molded in the format. Once the format is made, the insert is detached from the carrier and removed from the format leaving a precisely dimensioned capillary channel with an inlet and vent. A reagent may be applied in the capillary channel and the format used to measure the analyte in a fluid such as blood.

An electrochemical sensor with a capillary channel is formed by placing a sacrificial insert and electrodes on a sensor base and applying plastic material. After the plastic material is cured, the sacrificial is removed leaving a capillary channel in the sensor. The inserts may be removed by a tool including a clamp for clamping and holding each insert stationary and a sliding block to which the sensor is secured.

6 Claims, 7 Drawing Sheets

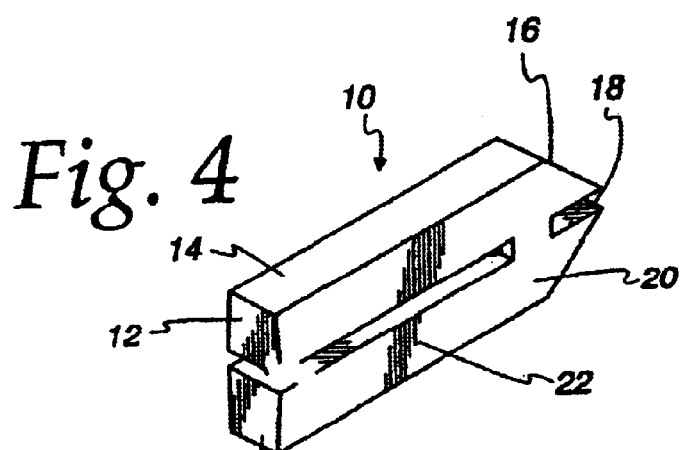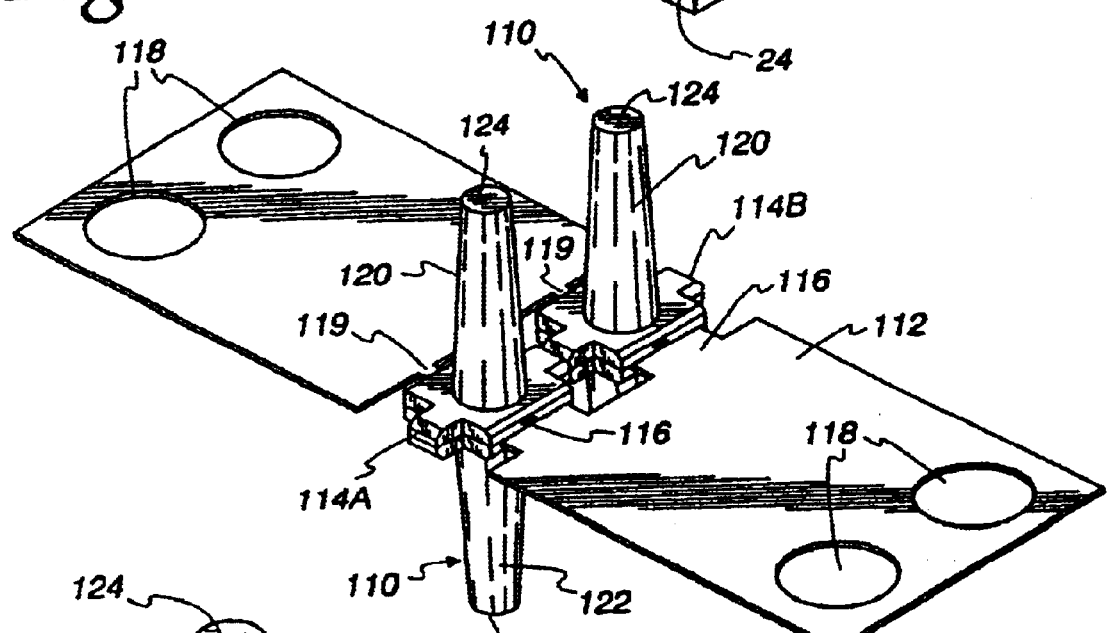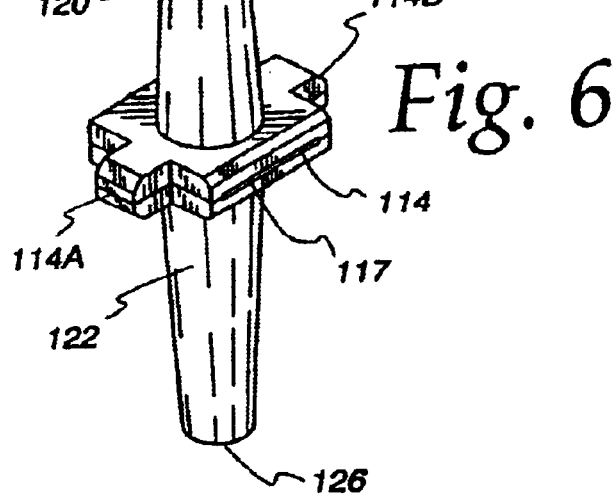

ELECTROCHEMICAL SENSOR

This application claims the benefit of provisional application 60/254,626, filed on Dec. 12, 2000.

FIELD OF THE INVENTION

The present invention relates to precision capillary channels for sensors and the method of making them.

BACKGROUND OF THE INVENTION

Sensors are used for sampling a fluid, mixing the fluid with a reagent, and making an analysis of the mixed sample. One form of sensor includes a capillary channel between two optical paths and a reagent in the channel. Another sensor is injection molded with a capillary channel between a base and lid. Electrodes and a reagent are located in the channel. A test fluid is drawn into the channel by capillary action and reacts with the reagent. In the first sensor, a light source is applied to one of the optical paths, and light from the light source is transmitted through the fluid in the channel and directed to a detector applied to the other optical path. In the second sensor an electric current acrossed the electrodes is measured.

A significant problem in the fabrication of optical reagent sensors is the production of a precision optical path length. This has been achieved by producing an optically clear part having a cavity of a certain depth. The cavity is covered by an optically clear lid. The precise depth of the cavity is difficult to produce repeatedly, but even if the depth can be repeatedly produced, it is very difficult to attach a lid and control the path length due to the tolerances of the method of attachment. In addition, if the attachment uses adhesives, variations in adhesives adds to the tolerances. Other types of attachment such as sonic welding each has their own variability.

The difficulty in repeatedly producing a cavity of a precise depth is critical when producing an optical reagent sensor that is to be used in the transmission mode. In the transmission mode the path length in the capillary gap is directly proportional to an analyte being tested. If an identical analyte is measured in two sensors that have different path lengths, the results reported will be different due to the path lengths. There is a need for a method of making optical reagent sensors with precise capillary channels that can be reproduced without variances or tolerances.

Similarly, the formation of a capillary channel in an injection molded sensor is difficult to produce. The usual way to fabricate sensors of this type is to precision screen print active areas within a capillary area formed by a shaped top lid. It is desirable to reduce the cost and assembly required by this construction. Moreover, it is difficult to provide electrodes in a small molded capillary channel of less than 0.005 inch in height and it is desirable to provide a sensor of this size with molded electrodes so that such a sensor could be used for electrochemical analysis.

SUMMARY OF THE INVENTION

The present invention is directed to an optical reagent sensor and an electrochemical sensor and to a method for making an optical reagent sensor and an electrochemical sensor. The optical reagent sensor includes a precision capillary channel with an inlet and a vent. To fabricate such a sensor, a carrier made of a material that is chemically etched, punched, die cut or otherwise formed to a predetermined configuration and with precision thickness is provided as an insert. An optical sensor is molded onto the carrier and once the molded material is cured, the insert is detached from the carrier and removed from the sensor leaving a precise capillary channel in the sensor. A reagent can be applied to the channel for a particular analyte to be tested. The sensor is used by drawing a test fluid into the capillary channel.

The electrochemical sensor of the present invention includes individual electrodes or contacts molded into the sensor. This process includes placing a first electrode in a base mold and placing a sacrificial insert in the mold above the first electrode. A second electrode is then placed in the base mold over the insert. A top mold is placed on the base mold and plastic material is injected into the top and base molds. After curing, the sensor is removed from the mold and the sacrificial insert is removed leaving a capillary channel with the two contact/electrodes in the channel.

Since the force required to remove the insert from the fabricated sensor could be quite high, it is desirable to use a tool that clamps the insert securely in place while applying a force on the sensor. The tool includes a clamp for clamping the insert in a stationary position and a moveable block to which the sensor is secured. A drive mechanism is coupled to the block to move the block relative to the clamp thereby withdrawing the insert from the sensor.

BRIEF DESCRIPTION OF THE DRAWINGS

Other objects and advantages of the invention will become apparent upon reading the following detailed description and upon reference to the drawings in which:

FIG. 4 is a reduced view of the sensor format illustrated in FIG. 3 with the portion of the carrier removed from between the legs of the format;

FIG. 5 is a perspective view of an alternative embodiment of the sensor format illustrated in FIGS. 1–4 on a carrier;

FIG. 6 is an enlarged view of the format illustrated in FIG. 5 with the carrier removed;

Figure 1:
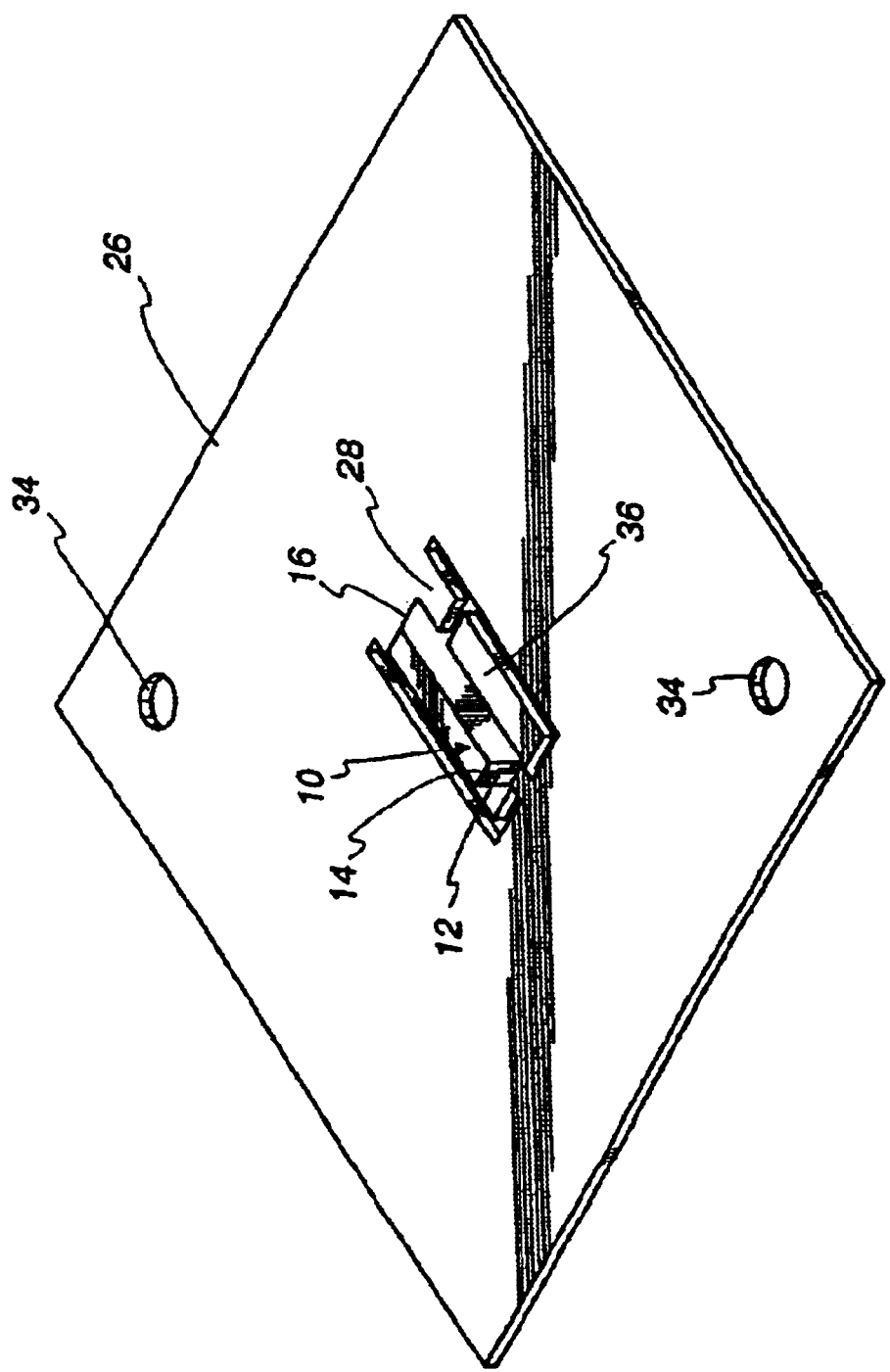
FIG. 1 is a perspective view of a sensor format on a carrier.
Figure 2:
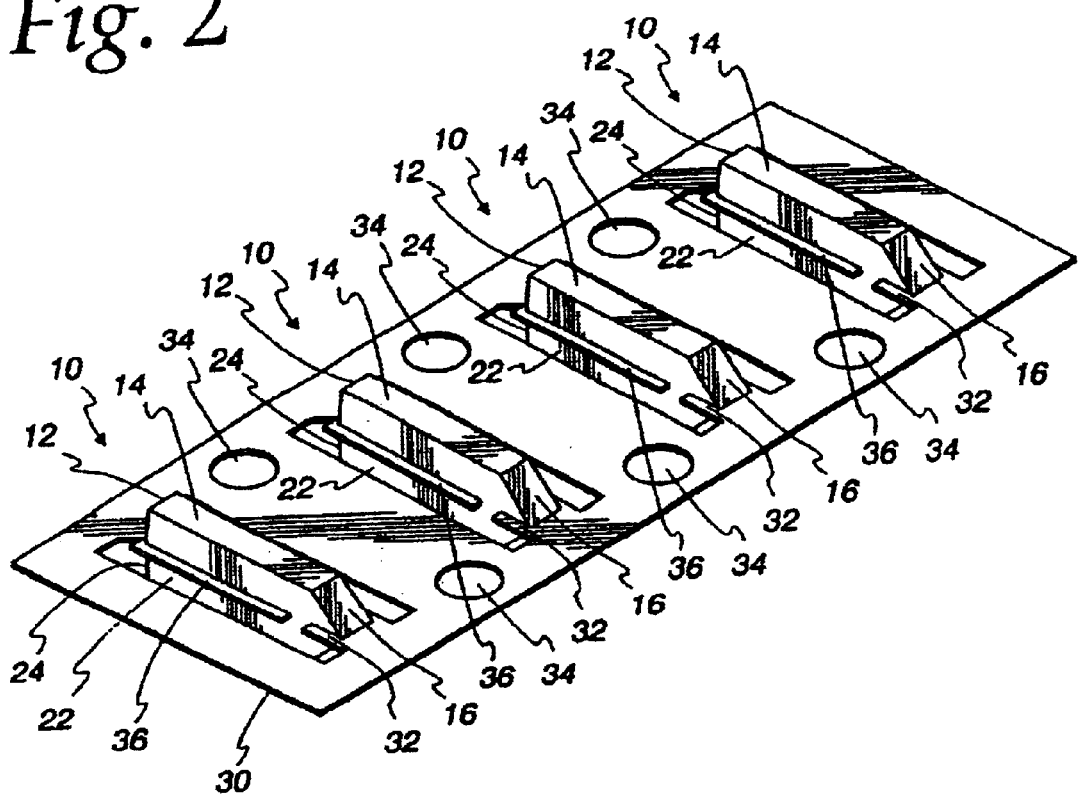
FIG. 2 is a perspective view of a chain of sensor formats on a carrier.

While the invention is susceptible to various modifications and alternative forms, specific embodiments thereof have been shown by way of examples in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

Referring to FIGS. 1–4, the sensor format 10 of the present invention is illustrated. The format 10 is an optical pipe formed of light transmission material. A light source is applied to an end 12 of a first leg 14 of the format 10. Light from the light source travels the length of the first leg 14 until it strikes a first end surface 16 that is at a 45° angle to the longitudinal axis of the first leg 14. The light is reflected by the end surface 16 through a capillary gap 18. Light that is not absorbed by material in the gap 18 strikes a second end surface 20 which is at a 45° to a longitudinal axis of a second leg 22 of the format 10. This light is reflected the length of the second leg 22 to a detector positioned at an end 24 of the second leg 22.

The format 10 is used in the transmission mode and the path length in the gap 18 is directly proportional to an analyte being tested. If the same analyte is measured in two different formats that have different path lengths, the results reported will be different due to the different path lengths. The format 10 of the present invention is made in a manner to insure a capillary gap 18 of a precise thickness for each format 10 to minimize or eliminate any differences reported due to different path lengths through the gap 18.

The format 10 is formed by injection molding over a single carrier 26 with an insert 28 or a multiple carrier 30 with multiple inserts 32. The single carrier 26 and the multiple carrier 30 are of a material, such as metal, that can be chemically etched, laser cut, mechanically punched, die cut or a similar fabrication process, to a known precise thickness and configuration required to form a precise capillary gap 18. The thickness of the carriers 26 and 30 are dependent on the desired light path length of the gap 18. The carriers 26 and 30 can be formed of materials whose melt temperatures are above the melt temperature of the format material and the carrier material must have sufficient tensile strength to allow removal of the inserts 28 and 32 from the format 10 after the format 10 has been molded.

To mold a format 10, the single carrier 26 and the multiple carrier 30 are positioned and secured in a molding tool by tractor feed or pin position holes 34. Plastic material is injected into the molding tool and the formats 10 are formed on the single carrier 26 and the multiple carrier 30. Once the plastic material is cured and the carriers 26 and 30 removed from the molding tool, the inserts 28 and 32 are separated from the carriers 26 and 30, respectively, and removed from the formats 10 leaving a precise capillary gap 18. Each gap 18 is of the same size and thickness due to the precision thickness and dimension of the inserts 28 and 32. A reagent can be wicked into each gap 18 and dried. If the gap 18 must be sealed on the sides, lids (not shown) can be secured to the sides of the format 10 without being part of the optical path.

Figure 3:
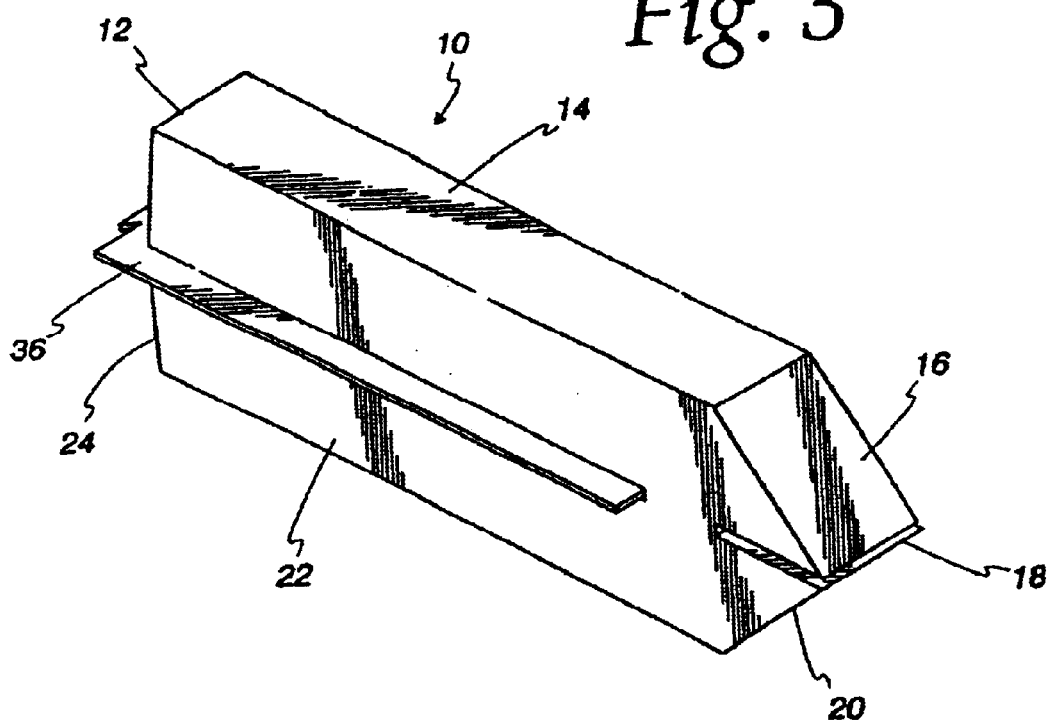
FIG. 3 is an enlarged view of a sensor format removed from a carrier with a portion of the carrier between the legs of the format.

An extension 36 of each carrier 26 and 30 extends between the first leg 14 and the second leg 22 of each format 10 and provides an opaque light barrier between the legs 14 and 22 or light paths (FIG. 3). The extension 36 also provides structural integrity to the legs 14 and 22 and the format 10. If a light barrier or structural integrity is not needed, the extension 36 can be removed from between the legs 14 and 22 (FIG. 4).

A format 110 that requires sides to be sealed and provides a direct optical read is shown in FIGS. 5 and 6. The format 110 is injection molded onto a carrier 112 in a manner similar to the molding of the reagent format 10 in FIGS. 1–4. The carrier 112 is of the same material as the carriers 26 and 30 and fabricated in the same manner to a known precise thickness to form a precise capillary gap 114. The gap 114 is formed by an insert 116 that is part of the carrier 112.

The carrier 112 is positioned in a molding tool by tractor feed or pin position holes 118, and casting material is injected into the molding tool to form the formats 110. After the casting material has cured, the carrier 112 is removed from the molding tool and the inserts 116 are extracted from the formats 110 leaving the precise capillary gaps 114 of micron sizes. There is an entrance or inlet 117 to each gap 114 and a vent formed by extensions 119 on carrier 112 on a side opposite the inlet 118. The gap 114 is enclosed on the sides 114A and 114B and sides or a lid is not required to form the gap 114.

The format 110 includes a first cone 120 above the gap 114 and a second cone 122 below the gap. The shape of the cones 120 and 122 can be any shape such as square and need not be the truncated cone shape shown in the drawings. A light source is placed at an end 124 of the first cone 120 and a light or optical detector is placed at an end 126 of the second cone 122. Light from the light source travels though the first cone 120 to an analyte in the gap 114, and light passing through the gap 114 and the analyte passes along the second cone 122 to the optical detector for measurement of the analyte or other specimen. The cones 120 and 122 isolate the optical components (light source and detector) from the gap 114 and the specimen in the gap to prevent contamination. If contamination is not an issue, the cones 120 and 122 can be eliminated.

Figure 9:
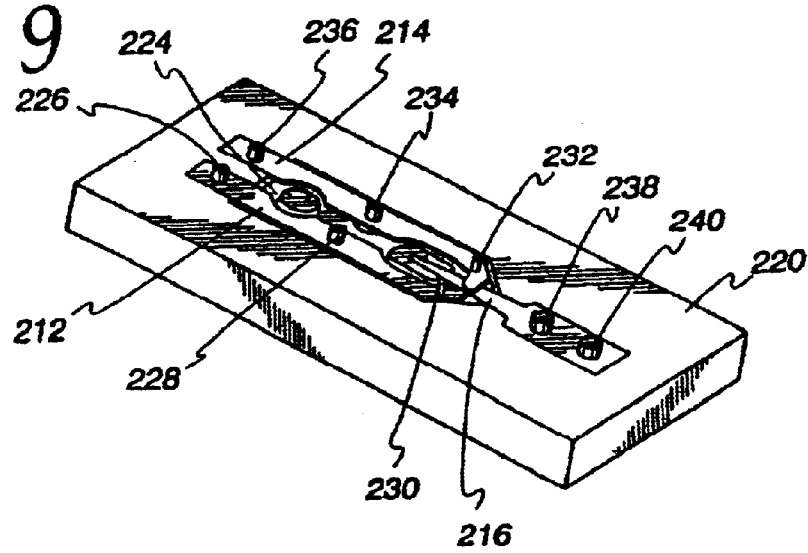
FIG. 9 is a view similar to FIG. 8 with a second contact positioned in the bottom mold.
Figure 10:
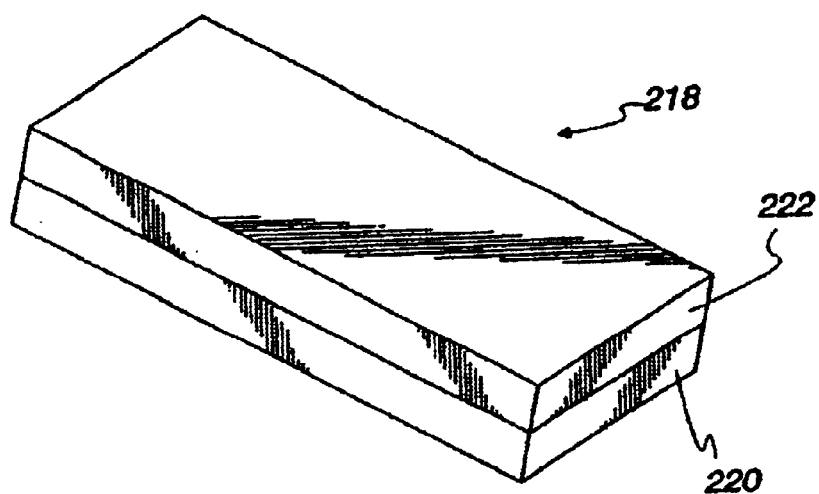
FIG. 10 is a perspective view of the molding tool with a top mold placed on the bottom mold.
Figure 11:
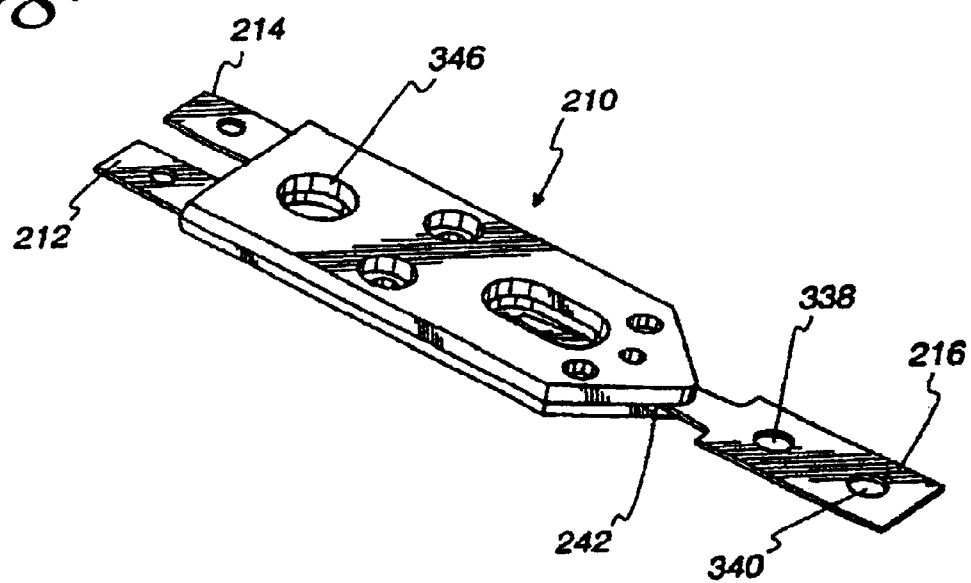
FIG. 11 is an enlarged perspective view of a molded electrochemical biosensor with a sacrificial insert in the biosensor.

Referring to FIGS. 7–11 an electrochemical sensor 210 is illustrated. The sensor 210 includes a first electrode 212 and a second electrode 214 molded into the sensor 210 (FIG. 11). The sensor 210 also includes a precise small capillary channel formed by a sacrificial insert 216.

The sensor 210 is injection molded in a molding tool 218 having a bottom mold 220 and a top mold 222 (FIG. 10). The bottom mold 220 (FIGS. 7–9) includes a cavity 224 in the shape of the sensor 210. A plurality of locator pins 226, 228, 230, 232, 234, 236, 238 and 240 are provided on the bottom mold for properly locating the first and second electrodes 212 and 215 and the sacrificial insert 216.

Figure 7:
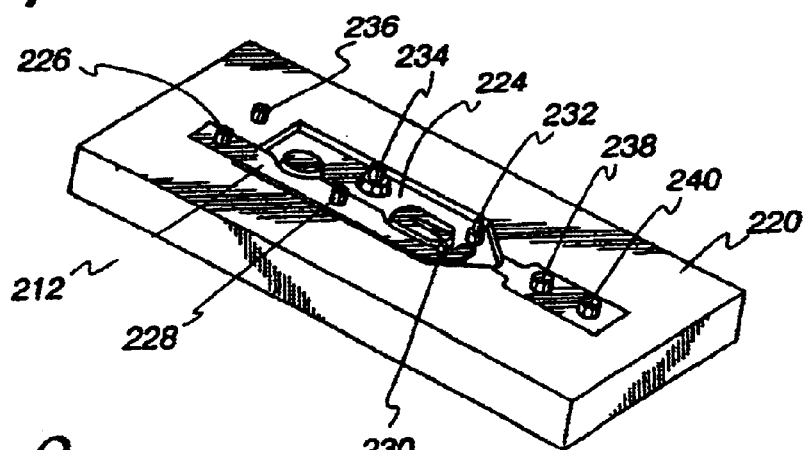
FIG. 7 is a perspective view of a bottom mold of a molding tool for molding an electrochemical biosensor with a first contact positioned in the bottom mold.
Figure 8:
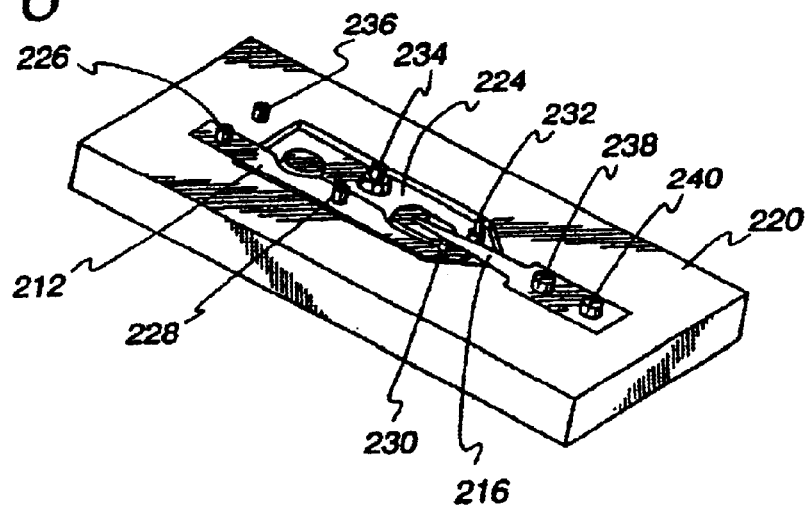
FIG. 8 is a view similar to FIG. 7 with a sacrificial protective insert positioned in the bottom mold.

The first and second electrodes 212 and 214 are loaded in the bottom mold 220 by stacking them such that the sacrificial insert 216 extends between them. The first electrode 212 is loaded first by fitting holes in the first electrode 212 over locator pins 226, 228 and 230 (FIG. 7). The sacrificial insert 216 is loaded next by fitting holes 238 and 240 in the insert over locator pins 238 and 240 (FIG. 8). The sacrificial insert 216 extends into the cavity 224 and over and on a forward end of the first electrode 212. The second electrode 214 is loaded in the bottom mold 220 onto locator pins 232, 234 and 236 with its forward end over and on the sacrificial insert 216 and over the forward end of the first electrode 212 (FIG. 9). The top mold 222 is then placed on the bottom mold 220 and compressed to provide compressive loading of both sides of the sacrificial insert 216. This compressive loading can be provided by raised portions in the bottom mold 220 and the top mold 222 that engage the sacrificial insert 216 between them as the top mold 222 is mounted on the bottom mold 220.

Once the molding tool 218 is assembled (FIG. 10), plastic material is injected into the tool 218. Due to the compressive loading, the cavity 224 is filled with plastic material but since plastic can not flow into the stack of the forward ends of the first and second electrodes 212 and 214 and the insert 216, the plastic material does not flow between the forward ends of the electrodes 212 and 214 and the insert 216.

Once the plastic material has cured, the molding tool 218 is opened and the sensor 210 with the first electrode 212 and second electrode 214 and the insert 216 are removed. The insert 216 is then removed from the sensor 210 leaving a precise small capillary channel 242 (FIG. 11) with the first electrode 212 on the bottom of the channel 242 and the second electrode 214 on the top of the channel 242.

Figure 13:
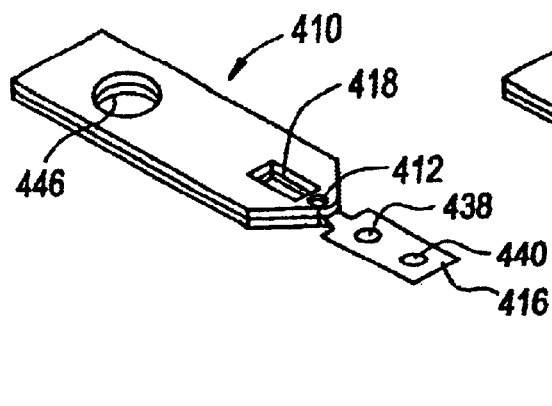
FIG. 13 is a perspective view of an optical sensor with an insert.
Figure 14:
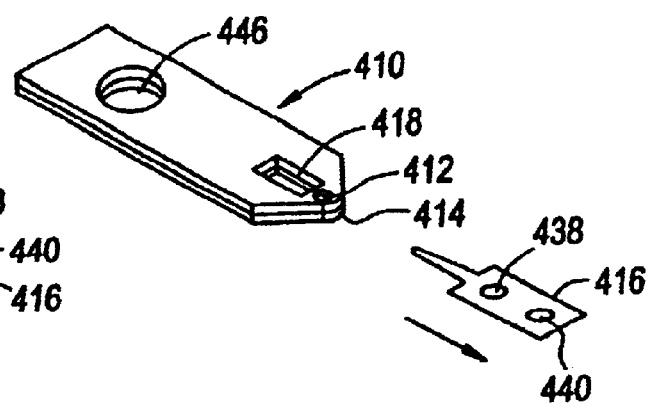
FIG. 14 is a view similar to FIG. 13 with the insert withdrawn.
Figure 15:
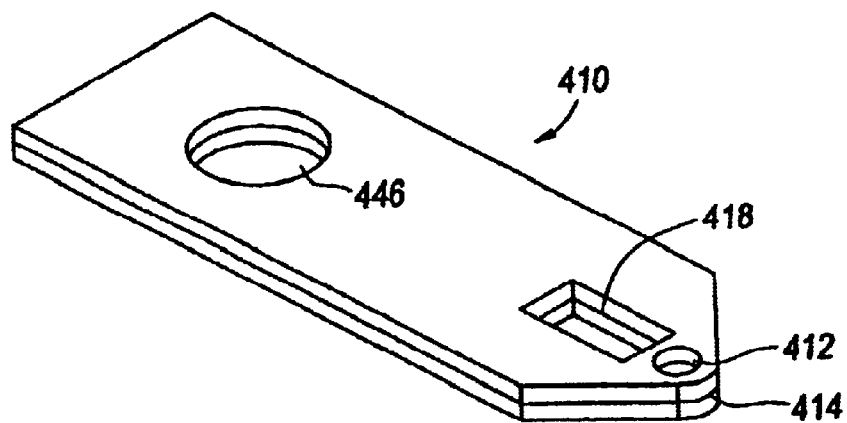
FIG. 15 is a perspective view of the optical sensor of FIG. 13.

An optical version of the electrochemical sensor 210 is illustrated in FIGS. 13–15. In these FIGS. 13–15 there is illustrated an optical sensor 410. The optical sensor 410 is molded in a manner and tool similar to that for the sensor 210 except instead of electrodes 212, 214, the optical sensor 410 includes an access window 412 for source optics and an access window for detector optics directly below the access window 412. A capillary cavity or channel 414 is formed in the optical sensor 410 between the access windows so that light from source optics directed into the access window 412 passes through a specimen in the capillary cavity or channel 414 and is read by detector optics positioned at the lower access window.

A mold or tool that forms the optical sensor 410 includes inserts that are highly polished and extend into the mold. As plastic material is injected into the mold, the plastic material flows around the inserts to form the access windows. Since the inserts are highly polished, the access windows are clear with little distortion.

The capillary cavity or channel 414 is formed by an insert 416 that may be made of stainless steel or similar material. The insert 416 is similar to the insert 216 in FIGS. 7–11 and includes fitting holes 438 and 440 that fit over locator pins similar to pins 238 and 240 in a mold (FIG. 8).

Because the insert 416 is very thin and large pressures occur in the mold during molding of the optical sensor 410, an access hole 418 is formed in the optical sensor 410 by a portion of the mold that grips the insert 416 and holds it stable as plastic material flows around the insert 416. The optical sensor 410 also includes a hole 446 similar to the hole 346 in the sensor 210.

Figure 12:
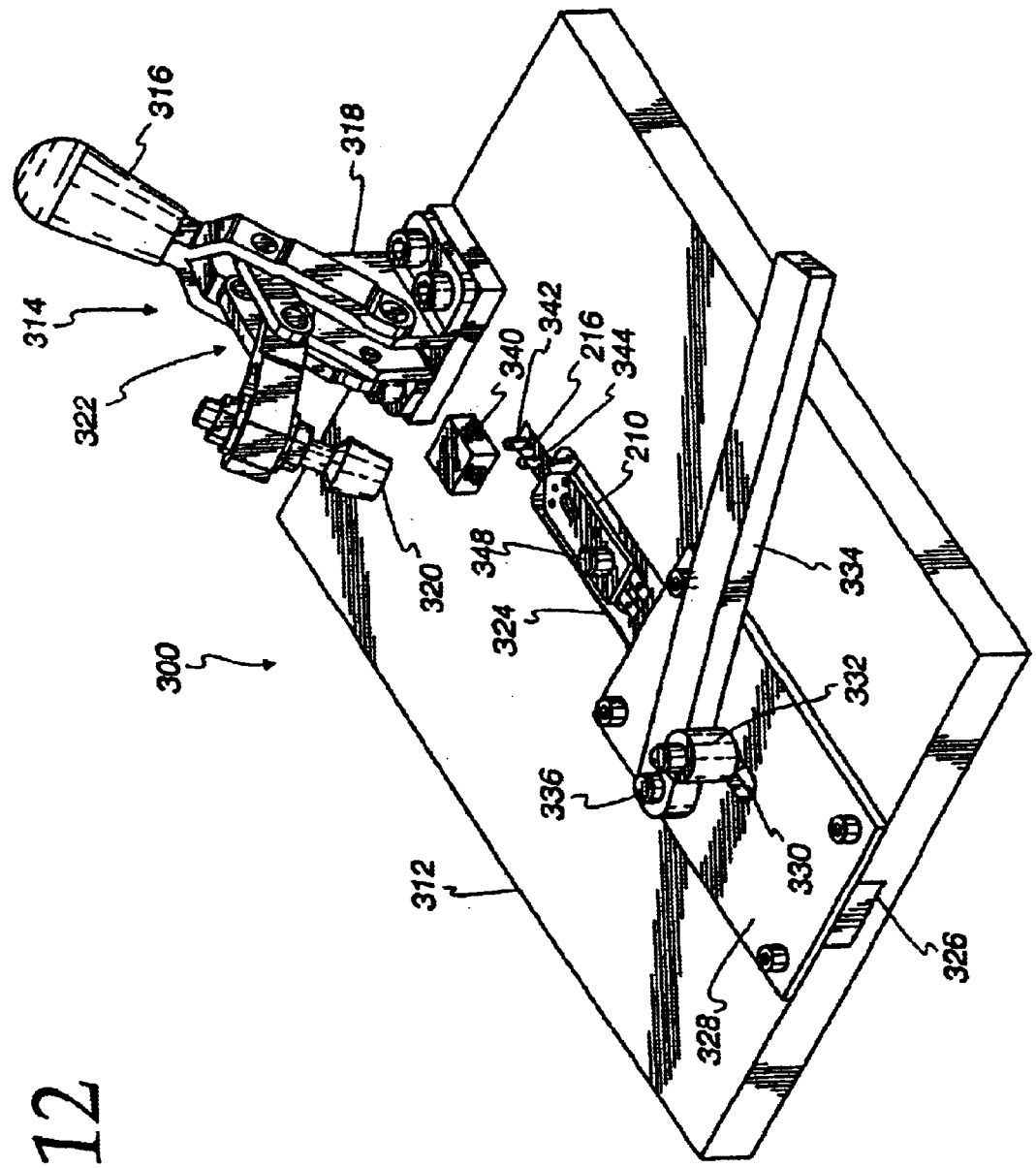
FIG. 12 is a perspective view of a tool used to remove the inserts from the biosensors illustrated in FIGS. 1–11.

In each of the above described embodiments the insert 28 or 216 must be removed from the sensor 14 or 210, respectively, and the force required to do this could be quite high. Therefore, it is desirable to have a tool that will hold the sensor 14 or 210 securely in place and supply sufficient force inline to the insert 28 or 216 to withdraw the insert 28 or 216 from the sensor 14 or 210. An insert removal tool or extractor 300 to accomplish these objectives is illustrated in FIG. 12. The extractor 300 is secured to a base 312 and includes a clamp 314. The clamp 314 may be a DeStaca clamp with a handle 316 pivotally mounted on a stand 318. The stand 318 is secured to the base 312. The handle 316 is coupled to a clamp head 320 by a linkage 322 such that rotating the handle 316 causes the clamp head 320 to move toward and away from the base 312.

The base 312 includes a cavity 324 in which is positioned a sliding block 326. A cover plate 328 is secured to the base 312 over a portion of the cavity 324. The cover plate 328 has a slot 330 through which extends a drive pin and bearing 332 that are attached to the sliding block 326. An extraction drive lever 334 is pivotally mounted on the base 312 by a pin 336 and abuts the drive pin and bearing 332 such that as the extraction drive lever 334 is pivoted in a clockwise direction about the pin 336 as view in FIG. 12, the drive pin and bearing 332 are moved in the slot 330 moving the sliding block 326 out the end of the cavity 324.

To remove an insert 28, 216 or 416 the sensor 14, 210 or 410 (in FIG. 12 sensor 210 is illustrated) is placed in the cavity 324 with the holes 238 and 240 (FIG. 11) in the sensor 216 placed over the pins 342 and 344 which are rigidly mounted on the base 312. A hole 346 (FIG. 11) in the sensor 210 is positioned over a sensor pin 348 on the sliding block 326. Accordingly, the sensor 210 is secured to the sliding block 326 and the insert 216 is secured to the base 312. A force distribution block 340 is placed over the pins 342 and 344 and clamped down onto the insert 216 by the clamp 314.

The insert 216 is withdrawn from the sensor 210 by a force inline with the sensor 210 and insert 216 by pivoting the extraction drive lever 334 to move the sliding block 326 in the cavity 324. This action pulls the sensor 210 away from the insert 216 cleanly withdrawing the insert.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An electrochemical sensor, comprising:
   a sensor base;
   a sacrificial insert on said sensor base;
   a first electrical contact and a second electrical contact in said sensor, said sacrificial insert positioned between said first electrical contact and said second electrical contact; and
   plastic material on said sensor base and over said sacrificial inserts said plastic material of a formulation which allows removal of said sacrificial insert from said plastic material and said sensor base leaving a capillary channel in said casting plastic material.

2. The sensor of claim 1 wherein the sacrificial insert is constructed of metal.

3. The sensor of claim 1 wherein the sacrificial insert is constructed of stainless steel.

4. The sensor of claim 1 wherein the insert comprises a material having a melt temperature higher than the melt temperature of the plastic material.

5. The sensor of claim 1 comprising a reagent disposed within the capillary channel.

6. The sensor of claim 1 wherein the sensor is adapted to analyze a liquid sample.

* * * * *